US010588814B1

(12) United States Patent
Engel et al.

(10) Patent No.: US 10,588,814 B1
(45) Date of Patent: Mar. 17, 2020

(54) ENHANCED VISUAL AND AUDIO CUEING SYSTEM FOR ROLLATORS

(71) Applicants: ATTI International Services Company, Inc., Hauppauge, NY (US); Eli Levi, Dix Hills, NY (US)

(72) Inventors: Richard Engel, Ridge, NY (US); Eli Levi, Dix Hills, NY (US)

(73) Assignee: ATTI International Services Company, Inc., Hauppauge, NY (US)

(*) Notice: Subject to any disclaimer, the term of this patent is extended or adjusted under 35 U.S.C. 154(b) by 0 days.

(21) Appl. No.: 16/008,257

(22) Filed: Jun. 14, 2018

(51) Int. Cl.
*A61H 3/04* (2006.01)
*A61B 5/00* (2006.01)
*A61M 21/00* (2006.01)
*A61B 5/11* (2006.01)

(52) U.S. Cl.
CPC ............ *A61H 3/04* (2013.01); *A61B 5/112* (2013.01); *A61B 5/4082* (2013.01); *A61B 5/7282* (2013.01); *A61B 5/746* (2013.01); *A61M 21/00* (2013.01); *A61B 2562/0204* (2013.01); *A61B 2562/0219* (2013.01); *A61H 2003/046* (2013.01); *A61H 2201/0188* (2013.01); *A61H 2201/5007* (2013.01); *A61H 2201/5097* (2013.01); *A61M 2021/0027* (2013.01); *A61M 2021/0044* (2013.01); *A61M 2230/63* (2013.01)

(58) Field of Classification Search
CPC ............ A61H 3/04; A61H 2003/046; A61H 2201/5097; A61H 2201/5007; A61H 2201/0188; A61B 5/112; A61B 5/746; A61B 5/7282; A61B 5/4082; A61B 2562/0204; A61B 2562/0219; A61M 21/00; A61M 2021/0044; A61M 2021/0027; A61M 2230/63
See application file for complete search history.

(56) References Cited

U.S. PATENT DOCUMENTS

| | | | |
|---|---|---|---|
| 2,719,568 | A | 10/1955 | Webb |
| 3,761,082 | A | 9/1973 | Barthel, Jr. |
| 4,256,098 | A | 3/1981 | Swan et al. |
| 4,303,041 | A | 12/1981 | Thompson et al. |
| 4,312,505 | A | 1/1982 | Engelhart |
| 4,770,410 | A | 9/1988 | Brown |
| 4,941,497 | A | 7/1990 | Prather et al. |
| 5,080,383 | A | 1/1992 | Hsieh |
| 5,112,044 | A | 5/1992 | Dubats |
| 5,137,501 | A | 8/1992 | Mertesdorf |
| 5,348,035 | A | 9/1994 | Porter |

(Continued)

*Primary Examiner* — Erez Gurari
(74) *Attorney, Agent, or Firm* — Brian Roffe (57) ABSTRACT

Walker including a frame, a movement enabling system on the frame that enables the frame to be moved along a surface, and a cueing system that generates audio and/or visual cues to enable a user of the walker to be guided in their forward movement of the walker. The cueing system includes a control unit that generates signals based on stored content relating to cue generation, at least one cue generator that generates the audio and/or visual cues based on the signals generated by the control unit, and a communications module coupled to the control unit and that receives via at least one communications frequency transmissions to set or modify the stored content. The control unit sets or modifies the stored content based on the transmissions received by the communications module.

32 Claims, 7 Drawing Sheets

(56) References Cited

U.S. PATENT DOCUMENTS

| | | |
|---|---|---|
| 5,397,171 A | 3/1995 | Leach |
| 5,526,893 A | 6/1996 | Higer |
| 5,538,268 A | 7/1996 | Miller |
| 5,575,294 A * | 11/1996 | Perry .................. A45B 3/00 362/102 |
| 5,772,234 A | 6/1998 | Luo |
| 5,813,948 A | 9/1998 | Quigg et al. |
| 5,893,367 A | 4/1999 | Dubats et al. |
| 6,439,250 B1 | 8/2002 | Balan |
| 6,742,523 B2 | 6/2004 | Dubats |
| 6,899,660 B1 | 5/2005 | Chin et al. |
| 7,484,740 B2 | 2/2009 | Miller |
| 7,814,866 B1 | 10/2010 | Gramza |
| 7,963,294 B1 * | 6/2011 | Trout .................. A61H 3/00 135/66 |
| 8,409,116 B2 | 4/2013 | Wang et al. |
| 8,663,133 B2 | 3/2014 | Johnson et al. |
| 8,702,567 B2 | 4/2014 | Hu et al. |
| 8,961,186 B2 | 2/2015 | LoSasso |
| 8,974,232 B2 * | 3/2015 | Behrenbruch ...... G06F 19/3481 434/258 |
| 9,062,986 B1 * | 6/2015 | Ellis .................. G01C 21/36 |
| 9,125,790 B2 | 9/2015 | Van Gerpen |
| 9,510,992 B2 * | 12/2016 | Fu .................. A63B 71/0009 |
| 9,675,515 B2 * | 6/2017 | Chou .................. A45B 3/04 |
| 9,801,437 B2 * | 10/2017 | Ho .................. A45B 3/04 |
| 2001/0045227 A1 | 11/2001 | Balan |
| 2004/0095251 A1 * | 5/2004 | Jackson ............ G08B 21/0446 340/686.6 |
| 2005/0183759 A1 | 8/2005 | Wolfe |
| 2006/0292533 A1 * | 12/2006 | Selod .................. A61H 3/02 434/247 |
| 2007/0034243 A1 * | 2/2007 | Miller .................. A61H 3/04 135/67 |
| 2007/0255186 A1 * | 11/2007 | Grill .................. A61H 3/00 600/595 |
| 2008/0053253 A1 | 3/2008 | Moore et al. |
| 2008/0251110 A1 * | 10/2008 | Pede .................. A61H 3/061 135/66 |
| 2009/0036815 A1 | 2/2009 | Ido |
| 2009/0292369 A1 | 11/2009 | Kazerooni et al. |
| 2010/0126542 A1 | 5/2010 | Pennise |
| 2010/0170546 A1 | 7/2010 | Popovic et al. |
| 2011/0023920 A1 * | 2/2011 | Bolton .................. A61H 3/04 135/66 |
| 2011/0118898 A1 * | 5/2011 | Fu .................. A61H 3/04 701/1 |
| 2012/0042917 A1 | 2/2012 | Workman et al. |
| 2013/0014790 A1 * | 1/2013 | Van Gerpen ........ A61H 3/04 135/66 |
| 2013/0171598 A1 | 7/2013 | LoSasso |
| 2014/0190536 A1 * | 7/2014 | Friedman ............ G08C 19/00 135/66 |
| 2014/0192516 A1 * | 7/2014 | Zimmerman ........ A45B 3/04 362/102 |
| 2014/0249452 A1 | 9/2014 | Marsh et al. |
| 2014/0265199 A1 | 9/2014 | Bagheri |
| 2014/0303508 A1 | 10/2014 | Plotnik-Peleg et al. |
| 2015/0115556 A1 | 4/2015 | Ledea |
| 2015/0283020 A1 | 10/2015 | Kim et al. |
| 2016/0166454 A1 | 6/2016 | Johnson et al. |
| 2016/0242392 A1 | 8/2016 | Holzworth |
| 2016/0253890 A1 | 9/2016 | Rabinowitz et al. |
| 2016/0287465 A1 | 10/2016 | Rabin et al. |
| 2016/0341410 A1 * | 11/2016 | Kohn .................. F21V 23/0464 |
| 2017/0007491 A1 | 1/2017 | Crombie et al. |
| 2017/0172462 A1 * | 6/2017 | Alghazi .................. A61G 5/10 |
| 2017/0175997 A1 * | 6/2017 | Rosenblum ........ H05B 37/0236 |
| 2017/0189258 A1 * | 7/2017 | Ott .................. A61H 3/04 |
| 2017/0231855 A1 | 8/2017 | Frazier |
| 2017/0231856 A1 | 8/2017 | Karlovich |
| 2017/0318976 A1 | 11/2017 | Journey |
| 2017/0352288 A1 * | 12/2017 | Weffers-Albu ...... G09B 19/003 |
| 2017/0354564 A1 * | 12/2017 | Dirauf ................ G08B 21/0476 |
| 2019/0105215 A1 * | 4/2019 | Dalley .................. A61H 1/024 |
| 2019/0125216 A1 | 5/2019 | Salcido |
| 2019/0133493 A1 | 5/2019 | Lien et al. |
| 2019/0150792 A1 | 5/2019 | Nakashima et al. |

\* cited by examiner

ENHANCED VISUAL AND AUDIO CUEING SYSTEM FOR ROLLATORS

FIELD OF THE INVENTION

The present invention relates generally to a mobility assistance device that could be used, for example, to provide mobility assistance to individuals living with a debilitating disease, in particular, Parkinson's disease.

BACKGROUND OF THE INVENTION

As many as one million Americans currently live with Parkinson's disease with approximately 60,000 more Americans diagnosed each year, not including thousands more that likely go undetected. Parkinson's disease is a neurodegenerative disorder often considered to be caused by a deficiency of dopamine in the basal ganglia circuit which leads to motor deficits. Kinesia paradoxa is a phenomenon most often seen in people with Parkinson's disease and although symptoms of Parkinson's disease are varied, one of the most affected motor characteristics is gait disturbance.

Festinating gait (also known as Parkinsonian gait) is characterized by a quickening and shortening of normal strides. Festinating gait can be disruptive for an individual diagnosed with Parkinson's disease and may interfere with the individual's ability to work and engage in daily activities. Furthermore, festinating gait can typically lead to accelerating gait which can result in an individual falling over and potentially causing injury.

One common symptom that affects roughly 50% of people in the advanced stages of the disease is referred to as Freezing of Gait (FOG). FOG is typically a transient episode that lasts less than a minute. During a FOG episode, gait halts with patients describing the situation as having his/her feet glued to the ground; when the patient overcomes the block, walking normally resumes.

Many Parkinson's patients use some form of wheeled walker (also known as a rolling walker or rollator) for mobility. Wheeled walkers may provide additional needed stability and are available in various configurations which can include a seat rest and hand brake(s,) and some can be equipped with optional sensory (visual/audio) cueing as described, for example, by Miller (U.S. Pat. Nos. 5,538,268 and 7,484,740). During a FOG episode, an individual using a wheeled walker with visual/audio cueing may press a button to display a laser line to step over and hear a series of metronome clicking to assist in overcoming the FOG episode. The visual/audio cueing has not really changed much since it was first adapted to wheeled walkers.

Of peripheral relation, U.S. Pat. Appln. Publ. No. 20130171598 and U.S. Pat. No. 8,961,186 (LoSasso) describe a system for improving movement in a user with impaired gait. The system includes a flexible front cross bar removably attached to a walker, and a first indicator attached to the front cross bar and having an indicator including electronic circuitry, a first light, and a first sensor. The first indicator provides a first visual cue. A second indicator is attached to the front cross bar and includes electronic circuitry, a second light, and a second sensor. The second indicator provides a second visual cue, which in combination with the first visual cue, instruct the user to move his or her legs in a particular order to improve a walking gait of the user.

Figures in LoSasso show the invention in use, for example, a relatively able-bodied individual using the walker for rehabilitation purposes. In addition to the first and second visual cues, such as a green glow of a ball that flutters and shimmers, auditory cues may also be provided, such as a pleasing and rewarding tone, only when one of the sensors is triggered. A controller enables transmission of data about the user's movement history, and also enables the visual and auditory cue settings to be controlled. LoSasso does not, however, enable remote control of the indicators.

Selod (U.S. Pat. Appln. Publ. No. 20060292533) describes a gait training system including an ambulation assist device such as a walker, and a target projection device (light source) attached to the walker which directs light to form a guide target in the path of the feet of the user. The user is able to select a number of light sources and a number of guide targets. Aural or tactile stimuli may be provided to accompany the guide target, e.g., a sound emitted from a speaker when the user steps on the guide target or a tactile stimulation provided by a vibrating handgrip.

Hu et al. (U.S. Pat. No. 8,702,567) describes a system for improving a user's movement and includes an assistive walking device having a frame that supports the user moving by foot across a walking surface, a first distance sensor attached to the frame and that determines a distance from an object crossing a line to the distance sensor, and a processor that determine characteristics of a gait the user based on the determined distance data. More specifically, the system of Hu et al. includes a first distance detector proximal to the user and the second distance sensor distal from the user and that are located orthogonally to the user on the side structure of the walker. During use, the user breaks the plane of the detector thereby rendering a sensing of user movement. Hu et al. does not enable remote control of the user-set characteristics of the system.

None of these references disclose remote initiation of visual/audio cueing, nor address safety when using a laser. None of these references disclose a system that is capable of adapting to changing gait through software. Moreover, audio is used as a form of feedback rather than as a prompt.

OBJECTS AND SUMMARY OF THE INVENTION

An object of at least one embodiment of the present invention is to automatically prompt the individual using the wheeled walker, either visually or audibly or both, rather than manually press a button to activate the visual and/or audio cues. Another embodiment of the present invention is to implement a moving visual cue line rather than a static or fixed visual cue line.

Yet another embodiment of the present invention is to implement a series of different colored visual cue lines rather than a static or fixed visual cue line. It is hypothesized that the movement and/or color variation may provide stronger stimulation to the brain in ways a fixed static laser line cannot.

Further embodiments of the present invention offer a series of tones, audio prompts or pre-recorded audio/sounds as an audible cue rather than a series of metronome clicking. It is also hypothesized that the addition of musical tones or voice prompts may stimulate the brain in ways a metronome click cannot.

Yet another object of the invention is to provide a wheeled walker with the ability to lock the brakes (by engaging the braking system) at the press of a button in the event of an episode of festinating/accelerating gait to prevent an individual from falling over. These embodiments may optionally be combined with other walker mobility aids (for example, a tether, braking system, etc.) to provide enhanced mobility and independence to individuals afflicted with Parkinson's disease.

The invention will be described in detail with reference to some preferred embodiments of the invention illustrated in the figures in the accompanying drawings. However, the invention is not confined to the illustrated and described embodiments alone.

BRIEF DESCRIPTION OF THE DRAWINGS

Additional objects of the invention will be apparent from the following description of preferred embodiments thereof taken in conjunction with the accompanying non-limiting drawings, in which.

DETAILED DESCRIPTION OF THE INVENTION

Wheeled walkers have been used for many decades as a way of providing increased mobility to people who find the daily task of walking a challenge. Initially, walkers started out as rigid frames and through incremental improvements over the years, are now foldable and can be equipped with seat, basket, wheels, brakes, etc. Newer improvements provide for increased stability and can be optionally equipped with hardware to address specific medical conditions such as Parkinson's disease. The invention disclosed herein seeks to address hardware that could be utilized for specific medical conditions such as Parkinson's disease using unique and novel approaches.

For the sake of clarity, all discussions will be directed to a fully wheeled walker—that is to say any portion of the walker that touches the floor/ground will have some form of fixed/free wheel or caster to allow movement, but the invention is in no way limited to a fully wheeled walker. So, generally, it will be considered that the walker integrating a safety system in accordance with the invention includes a movement enabling system on a frame of the walker that enables the aid frame to be manually moved by the user along a surface. The movement enabling system may include the wheels or casters at each portion that contacts the surface or only a portion thereof. Indeed, in a preferred embodiment the disclosed invention could be retrofitted to an existing walker.

Figure 1:
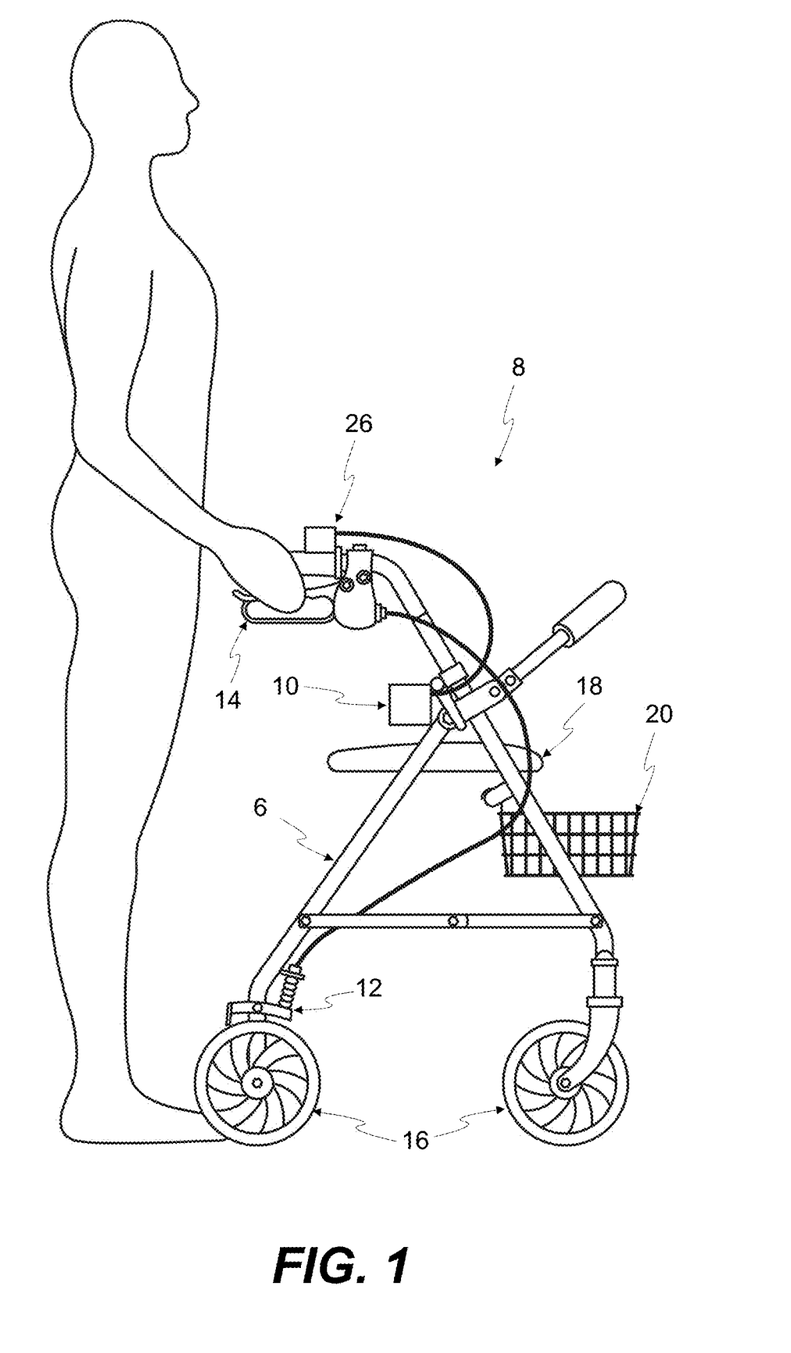
FIG. 1 shows an individual using a typical wheeled walker equipped with an enhanced cueing control unit.

FIG. 1 reflects a garden variety wheeled walker 8 that is commonly available at the time of this application which has been retrofitted with an enhanced cueing system. The walker 8 includes a frame 6, brakes 12 actuated by a braking mechanism 14 for each hand to better control the movement of the walker 8. Walker 8 also includes wheels 16 on a lower portion of the frame 6 of the walker 8 (the movement enabling system), an optional seat 18 attached to the frame and an optional basket 20 also attached to the frame 6.

In accordance with the invention, the walker 8 includes an enhanced cueing control unit 10 that is centrally located between the structure of wheeled walker 8 and the individual using the walker 8 and serves as the central decision-making element. This position may be interpreted to mean that the enhanced cueing control unit 10 is attached to the frame in a position in which it is rearward of the portion of the frame 6 to which it is mounted, as shown in FIG. 1. This position is not limiting and the criteria for placement of the enhanced cueing control unit 10 is that it should be located in a position easily accessible to the user of the walker 8.

Figure 2:
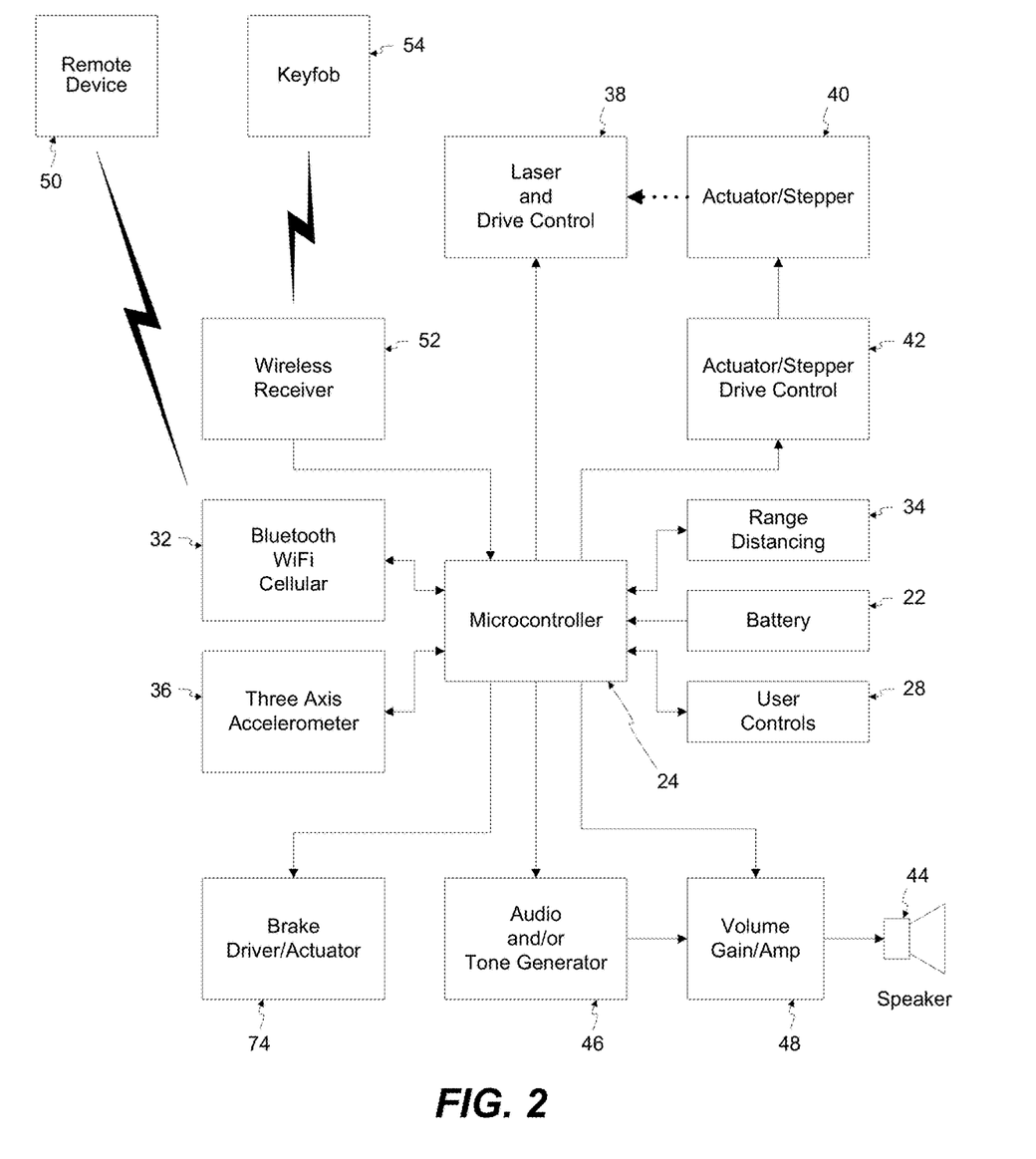
FIG. 2 depicts a block diagram of the enhanced cueing control unit in accordance with the invention.

The control unit 10 comprises a number of varied components as shown in FIG. 2, each of which will be described in detail as to purpose and operation. The components represented schematically may be conventional off-the-shelf components known to those skilled in the art to which this invention pertains. Also, the components may be housed in a common housing, shown as the box in FIG. 1, or some components may be arranged at different locations on the frame 6.

In a preferred embodiment, the control unit 10 utilizes a rechargeable style battery 22 as a source of power although alternate embodiments of the invention could utilize a conventional style battery, such as alkaline, silver oxide, carbon zinc, etc. The battery 22 would supply power for the entire enhanced cueing system. The enhanced cueing system is controlled by a central microcontroller 24 connected to the remaining components and which gathers status and information from the surrounding support peripherals. Alternate embodiments may substitute a microprocessor and support hardware in lieu of the microcontroller, and all are considered to be encompassed within the recitation of a controller.

Figure 3:
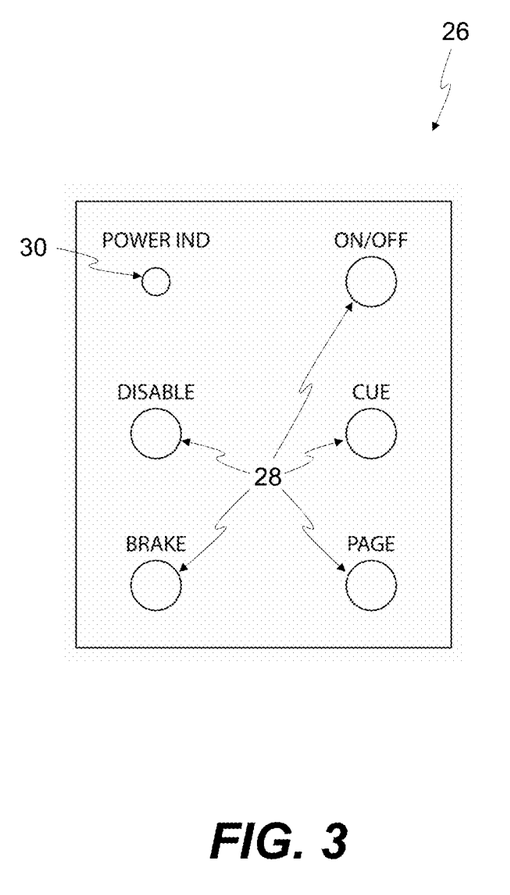
FIG. 3 illustrates a sample user control panel.

A user control panel 26 for the enhanced cueing system is illustrated in FIG. 3 is designed with a minimalist interface so as not to be confusing. The user control panel 26 comprises a plurality of switches or buttons and indicators, generally referred to as user controls 28, see FIG. 2. Switches may be used for functions such as: On/Off, Cue, Disable, Page (Emergency), Brake, etc. Indicators 30, one of which is shown in FIG. 3, would be implemented as light emitting diodes (LEDs) and be of single color or multi-color varieties.

A plurality of near field communication (NFC) or personal area network (PAN) communications hardware serve various overlapping functions, represented by 32 in FIG. 2. This hardware 32 covers short range communications such as Bluetooth, mid range communications such as WiFi, ISM (industrial, scientific and medical) or LoRa (long range) wireless spectrum radio bands or wide range communication networks such as commercial cellular networks. Due to the overlapping nature of these communication methods, it should be assumed that any one of these methods could be used. One skilled in the art would understand what hardware is necessary to obtain the desired communications functionality. This hardware 32 may be included in the same housing as the control unit 10.

Range distancing hardware 34, such as an ultrasonic detector, forms the basis for sensing the distance between the individual using the wheeled walker 8 and the structure of the walker 8 itself, i.e., the frame 6. A three axis accelerometer 36 can be used both for motion sensing as well as positional/orientation of the structure or frame 6 of the walker 8.

Visual cueing is provided by a laser line generator 56 (see FIG. 4A) and its associated drive control hardware forming a laser line generator module 38 (see FIG. 2) which can be turned on or turned off (aka 'blanked') instantaneously.

Laser line generator module 38 may be arranged on the frame 6 in a position in which a laser line generated by the laser line generator 56 of the laser line generator module 38 is projected in front of the feet of the user of the walker 8.

Current requirements may necessitate the need for drive circuitry in the form of a relay or solid state switch (e.g., BJT or MOSFET). A linear actuator or stepper motor 40 provides for the sweeping arc movement that is projected in front of the individual, controlled by an actuator/stepper drive control 42 based on commands in the form of signals from the microcontroller 24. Other movements may be provided by the linear actuator and stepper motor 40, or comparable actuators or motors, and configuration of the linear actuator or stepper motor 40 or other type of actuator or motor to provide such alternative movements is within the purview of one skilled in the art to which this invention pertains. The drive control 42 may be configured to provide the desired motor control. Current requirements may necessitate the need for drive circuitry in the form of relays or solid state switches that form an 'H' bridge to provide bidirectional movement within the intended arc.

Audio cueing is provided via an audio generator, such as, but not limited to, speaker 44. The speaker 44 may be driven by a tone generator and/or audio generator 46 that has programmable volume control in the form of Volume Gain/Amp 48, and is controlled based on commands in the form of signals from the microcontroller 24. Speaker 44 and tone generator and/or audio generator 46 may be arranged in a common housing together with other components of the control unit 10 or separately, e.g., in a second housing on a different part of the frame 6, possibly closer to the handles. Speaker 44, tone generator and/or audio generator 46 and Volume Gain/Amp 48 may be referred to collectively as a sound generating module.

Generally, the tone generator and/or audio generator 46 will be referred to as an audio generator and is any component, or group of components that cooperate, that receive commands embodied in electrical or electronic signals and cause generation of specific sounds (whether musical notes, words, etc., and combinations thereof) based on the commands. In a preferred embodiment of the audio generator 46, this function would be capable of producing not only tones but playing stored audio files accessed by or stored in memory available to the audio generator 46. These files could be pre-stored (aka 'canned') files or audio files that have been customized for a specific individual. As used herein, any of the sounds generated by the audio generator 46 will be referred to as a sound tracks, which may be music, words, combinations thereof, and any other sounds.

To achieve this, one or more memory components are connected to or integrated into the microcontroller 24 and contain audio files that are vocalized by the audio generator 46 to be output from the speaker 44 upon command from the microcontroller 24, i.e., the microcontroller 24 directs commands to the audio generator 46 to cause specific audio files to be vocalized by the speaker 44. Additionally, the microcontroller 24 generates commands to manage the audio files in the memory component.

Management of the audio files in the memory component entails, but is not limited to, adding audio files, deleting audio files, change the audio files to be vocalized, etc., and may be achieved by the microcontroller 24 processing transmissions received by the near field communication (NFC) or personal area network (PAN) communications hardware component 32. The microcontroller 24 is the intermediary between the near field communication (NFC) or personal area network (PAN) communications hardware component 32 and the audio generator 46 and to this end, converts the audio file management commands derived from the received transmissions into control signals and then effects the requested changes to or of the audio files in the memory component(s).

Alternate embodiments may limit the audio generator 44 to simple tone generation. Other embodiments may implement this function directly within the microcontroller 24 rather than as a separate hardware function. A volume gain/amplifier system 48 drives the speaker 44 upon command from the microcontroller 24 and modifies the audio and/or tone being generated by the audio generator 46.

The enhanced cueing system can be adapted to a wide range of individuals using software configurable parameters that can be uploaded to the enhanced cueing system. These parameters can be modified using the NFC/PAN hardware 32 within the invention when coupled with a consumer smart device (e.g., cell phone, tablet, laptop or other similar device) herein referred to as the remote device 50. These parameters would typically be entered/uploaded by a trained professional versed in the areas of Parkinson's disease and gait related issues. A downloadable application (aka 'app') on the remote device 50 would permit customization to tailor operation to each individual's needs. In a preferred embodiment, the remote device 50 would have the ability to configure parameters, download customized audio files and provide the ability to interact with the operation of the enhanced cueing system using the NFC/PAN communications support hardware 32.

The invention therefore also encompasses a software program that is resident on the remote device 50 and provides functionality to define parameters for use of the audio generator 46 as well as attendant characteristics of sound being generated by the audio generator 46, e.g., parameters of the gain/amplifier component 48, and generally control what, when and how sound is generated by the audio generator 46. Using the computer program on the remote device 50, the user would be able to add audio files, delete audio files, record audio files using a microphone on the remote device 50, with these audio files being those in one stored of the memory components accessed by the microcontroller 24 during operation.

The computer program on the remote device 50 would also be capable of enabling the user to control any other variable parameters of the cueing system, including, the visual cueing provided by the laser line generator module 38. Thus, the computer program would enable the user to determine the manner in which the laser line generator module control operates (in any of the various configurations described below) and the range distancing hardware 34 parameters.

The computer program may be configured to provide information to the user about the cueing system, such as the currently set audio and visual cueing parameters, to enable the user to determine whether any need to be changed, the status of the battery 22, the status of the user controls 28, the status of the range distancing hardware 34, and the status/functionality of other components. In this manner, by using the computer program at the remote device 50, a user would be able to obtain information about the cueing system and adjust its operation whenever desired, all remotely using the communications connection provided by the PAN/NFC communication system 32.

Remote device 50 is not limited to any device disclosed above and may be generally any component that is capable of communicating with the PAN/NFC communication system 32 and capable of receiving instructions by a user to effect control of the cueing system. The remote device 50 may be portable, like a smart phone, laptop, tablet, and personal data assistant, or what are generally considered a non-portable device like a mainframe computer. Indeed, it is possible to have a single remote device 50 controlling multiple cueing system on multiple walkers, e.g., a central control facility for people using walkers which may be useful in an assisted living facility, hospital or nursing home. Accordingly, there is not required to be a dedicated remote device 50 for each control unit 10.

One of the items on the user control panel 26 would be a On/Off (power) switch. This switch would be arranged such that after a prolonged period of inactivity, the enhanced cueing system would automatically power down to conserve power of the battery 22. The period after which the enhanced cueing system shuts down after inactivity is one of the parameters defined via the remote device 50 and stored in EEPROM associated with or accessible by the microcontroller 24. EEPROM is used herein as an example of a memory component and any other comparable memory component may be used in the invention. The hardware includes the ability to monitor battery capacity or remaining battery life (aka 'gas gauge') which may be conveyed via a tri-color (green/yellow/red) power indicator LED as part of the user control panel 26 (see FIG. 3). The battery life information can also be mirrored to the remote device 50 for additional monitoring capability, or additionally or alternatively to another remote device.

There is no definitive consensus as to whether continuous cueing vs. induced cueing (only during a FOG episode) provides beneficial improvement for individuals suffering from frequent FOG episodes. Prior art from Miller, identified above, requires cueing to be manually initiated by the individual by pressing a button, capacitive sensor or solid state strain pressure sensor. By contrast, in one embodiment of the invention, sensory cueing (visual and/or audio) is provided on a continuous basis once power is applied to the enhanced cueing system.

In such an embodiment, the activated components of the cueing system, i.e., the audio generator 46 and the laser line generator module 56, are coupled to the battery 22 either indirectly through the microcontroller 24 as shown in FIG. 2 or directly without interposition of the microcontroller 24. As soon as the cueing system is turned on, e.g., using the on/off switch of the user control panel 26 shown in FIG. 3, the audio generator 46 generates audio cues and/or the laser line generator module 38 generates visual cues. The cues are continuously generated, i.e., they do not stop until the on/off switch of the user control panel 26 is depressed or the Disable switch or button on the user control panel 26 is depressed or otherwise activated.

Continuous generation of the cues does not depend on the occurrence of a FOG episode but rather is simply the continual generation of cues irrespective of whether the user of the walker 8 is experiencing a FOG episode. By continuously generating cues, the cueing system and a walker including the same does not rely on the user to feel that they are about to experience a FOG episode and then activate the cueing system or rely on sensors to detect the occurrence of a FOG episode. As such, the cueing is immediately available to the user as soon as the FOG episode begins.

The manner in which continuous cueing is achieved may be by providing an electrical circuit including the battery 22 and the audio generator 46 and/or laser line generator module 38, with the on/off switch being activated into the on position to complete the electrical circuit. One skilled in the art would readily understand how to implement the "continuous on" cueing system in view of the disclosure herein and knowledge of electrical circuits.

As an alternative to continuous cueing, the enhanced cueing system can be designed to sense a FOG episode through the use of range distancing via range distancing hardware 34, also referred to as a range distancing module. The range distancing hardware module 34 provides the distance to the microcontroller 24 that can be correlated to the occurrence of a FOG episode.

In a preferred embodiment, the range sensing is initiated (induced) using an ultrasonic sensor due to low cost and widespread availability. Ultrasonic frequencies are generally considered to be frequencies above the nominal human hearing range of 20 Hz to 20 kHz, usually in the range of 28 kHz to 200 kHz with a nominal frequency of 40 kHz being quite common. Alternate embodiments might utilize other proximity sensing technologies (e.g., radar, RSSI from cell phone) but the intent is the same—to sense the distance between the individual and the structure of the walker 8. Multiple technologies may be used for range distancing hardware on a redundant basis.

In a preferred embodiment, distance is calculated based on round trip time delta between the initial transmit (TX) pulse and received (RX) echo return pulse using the calculation:

$$D = 0.5 * c * T$$

where:
D=distance
c=speed in medium (air)
T=time delta between TX pulse and RX echo In air (at 0° C. and little humidity) the speed is generally accepted as:

$$c = 331.3 + (0.606 * T_C) \text{ meter/sec}$$

where $T_C$ is temperature in degrees Celsius.

Microcontroller 24 then determines whether the user of the walker 8 is experiencing a FOG episode based on changes over time in the distance (D) between the walker and the user. For the ultrasonic embodiment, it is presumed that the ultrasonic transmitter of the range distancing module 34 is directed to a location at which part of the user's body will be present to enable this part to reflect ultrasonic waves transmitted by the ultrasonic transmitter. In this case, it can be presumed that the object in the path of the ultrasonic waves is the user of the walker 8 (otherwise the distance reading would not have any bearing on data about the user of the walker 8). Moreover, the ultrasonic receiver of the range distancing module 34 is positioned in an expected path of the transmitted waves that are reflected by the user. It is possible to co-locate the ultrasonic transmitter and receiver and orient them rearward from the frame 6 of the walker 8 to a location at which the user will invariably occupy while using the walker. The selected location would be readily determinable by those skilled in the art to which this invention pertains without undue experimentation.

Microcontroller 24 may be programmed to determine a pattern of change in the distance between the walker 8 and the user based on multiple determinations of the distance between the walker 8 and the user, obtained via the range distancing module 34. Microcontroller 24 then determines that the user of the walker 8 is experiencing the FOG episode based on a deviation from the pattern. The pattern may be unique to the user and derived from data about use of the walker 8 by the user.

Accuracy of the ranging is not critical; what is more important is the rhythmic increasing/decreasing of the distance between the individual and the walker structure and as such the temperature portion can largely be ignored. This rhythmic cadence depends on a number of factors such as walking speed (nominal, minimum, maximum), spatial distances involving the enhanced cueing control unit 10 and individual (nominal static, minimum, maximum distance), movement time threshold and other factors which are unique to an individual. These factors would be entered into the enhanced cueing system via the remote device 50 and stored in electrically erasable programmable read only memory (EEPROM) contained within the microcontroller 24. They could alternatively be derived from sensors on the walker 8.

In a preferred embodiment, these factors would serve as an initial starting point, and a computer program executed by the microcontroller 24 would adaptively refine (or 'learn') these settings and either overwrite them or create a secondary set of parameters that are continuously refined. The conditions for overwriting the initial set of parameters in memory as the stored content used by the microcontroller 24 to generate cues may be derived from the distance determinations or data from other sensors on the walker 8, and a program that generates modified parameters based on the determined distances, data or other use of the walker 8 provided in the cueing system 10. Alternate embodiments may implement EEPROM that is not embedded within the microcontroller 24. This distance would be polled on a regular periodic basis (e.g., once every half second) which is also one of the factors that would be programmed through the remote device 50 to continually determine the distance between the individual and the wheeled walker 8.

The rhythmic walking cadence sensed within the enhanced cueing control unit 10 may be utilized to identify potential FOG episodes when the lack of rhythmic movement exceeds a movement time threshold which may be predetermined or determined by the microcontroller 24 based on the input from, for example, the remote device 50, based on a deviation in the rhythmic movement relative to a permitted range of deviation Microcontroller 24 could determine the rhythmic walking cadence (rhythm) for the distance between the walker 8 and the user based on multiple determinations of the distance between the walker 8 and the user (obtained using range distancing module 34) and data about the user provided in transmissions received by the PAN/NFC communication system 32 after entry via the remote device 50. Upon the microcontroller 24 sensing a potential FOG episode (based on lack of rhythmic movement relative to the threshold or deviation beyond a permitted deviation range), the enhanced cueing system would automatically initiate visual and/or audio cueing via the laser line generator module 38 and/or speaker 44, respectively, to assist the individual.

A computer program executed by the microcontroller 24 monitors the user's movement, derivable from the distance measurements provided by the range distancing module 34, and then determines the presence of lack of movement relative to the threshold or deviation beyond a permitted deviation range, and then generates and directs a command to the audio generator 46 and/or the laser line generator module 38 to generate audio and/or visual cues, respectively.

The visual and audio cueing systems can be individually enabled/disabled via the remote device 50 and these settings are retained in EEPROM as well. A software program at the remote device 50 presents the user with the possibility to independently or in combination, enable and disable the audio generator 46 and the laser line generator module 38. When the user enters a command via a user interface of the remote device 50 to effect the disable or enable of a cue system, the remote device 50 generates the corresponding command and signals using wireless communications frequency to the cueing system to effect the desired control commands.

A plurality of options for manually initiating visual and/or audio cueing is provided. This manual initiation can be effected by the individual using the walker 8 by pressing a momentary pushbutton Cue switch on the user control panel 26 (see FIG. 3). Manual initiation can also be initiated by another individual (e.g., a caregiver, family member) to allow observation/intervention from a distance which affords the individual some semblance of independence and in turn, spares the humiliation of requiring others to continually step in and intervene to aid the person using the walker 8.

In the manual mode, whereby the caregiver initiates cueing, this initiation can be effected through PAN/NFC communication using the remote device 50 or through the wireless receiver 52 using a pushbutton on a battery powered key fob pushbutton 54 (see FIG. 2). In a preferred embodiment, this key fob 54 would employ address selection and code-hopping code similar to remote keyless entry (RKE) or that of a garage door opener to avoid interference with other potential users.

Cueing, whether initiated by the range distancing or manually, may comprise one or more cycles of visual and/or audio cueing. The number of cycles would be a definable parameter that is set via the remote device 50 and stored in EEPROM. In a preferred embodiment, the individual can press a Disable switch or button on the user control panel 26 to inhibit the cueing functions in the event the individual voluntarily stops (becomes fatigued and needs to rest) or is frustrated by continuous cueing, see FIG. 3. A short press (e.g., less than two seconds) on the Disable switch or button would temporarily disable cueing for a set period of time (defined via the remote device 50 and stored in EEPROM) whereby a long press (e.g., greater than three seconds) on the Disable switch or button would disable cueing until another long press is sensed or power has been cycled on the enhanced cueing system.

The enhanced cueing system also includes a "Page" button on the user control panel 26 which serves as a way of alerting another individual (e.g., caregiver, family member) in the event the individual using the walker 8 is unable to do so, see FIG. 3. This page function can send a message to a remote device (the same as or different than remote device 50) through PAN/NFC communication system 32. This page function could be used to alert a nearby individual as a request for assistance using a short button press or as an emergency notification using a long button press.

The page button may be considered an example of an actuatable member, since it may be substituted for by a switch, slider and the like, and that, when actuated, sends a general, predetermined or pre-programmed alert to one or more remote alert receiving devices. The specific remote alert receiving devices, and the alerts sent thereto, may be programmed by the user or their caregiver. Although preferred, it is not required that the alerts be sent using the PAN/NFC communications system 32 and other communications techniques between the user control panel 26 and the remote alert receiving devices may be employed.

In one embodiment, the actuatable member (page button) is actuated in a plurality of different ways, e.g., short button press or long button press as mentioned above, and depending on how the actuatable member is actuated, one a plurality of different alerts is sent to the remote alert receiving device(s). This introduces another variable to the possible alerts, i.e., it is possible to pre-program not only the alerts or messages and the remote alert receiving devices, but also associate a different button press with a specific alert and one or more specific remote alert receiving device(s). That is, a short button press may cause a request for assistance to a caregiver while a long button press may cause an emergency notification to a 911 facility and the user's family.

In the event of an emergency situation, the speaker 44 within the enhanced cueing system can be configured to sound an alarm alerting other nearby individuals to the emergency. The enhanced cueing system also has the ability to notify one or more other individuals (e.g., caregiver, family member) via short message service (SMS, aka 'text message') and/or other similar communication means in the event the emergency notification has been initiated. As with the other programmable parameters, notification contact information (e.g., cell phone number) could be entered via the remote device 50 and stored in EEPROM. The PAN/NFC communications system 32 may be used for the emergency notification messages or the emergency notifications may be sent by other communication means. Alternate embodiments may include global positioning system (GPS) capabilities to identify an individual's location as pass that information along as well. These locating systems may be considered integrated into or part of the PAN/NFC communication system 32.

Figure 4A:
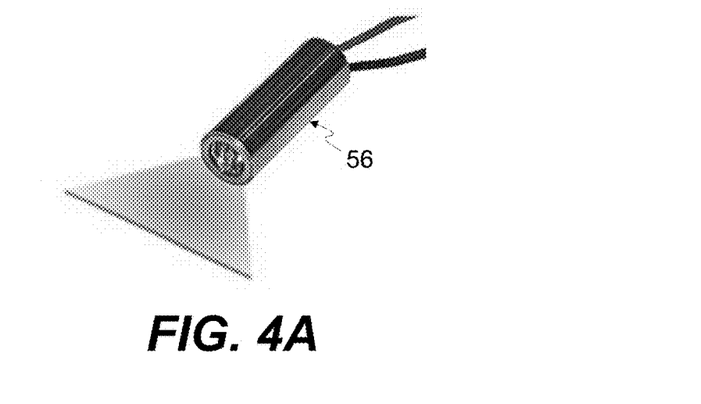
FIG. 4A reflects a sample laser line generator module.

The visual cueing function of the enhanced cueing system centers around a laser line generator 56 as depicted in FIG. 4A (part of the laser line generator module 38). Inexpensive, readily available laser line generators and modules including the same include as primary components, integrated wave lens, collimating lens, laser diode, and driver circuit. Depending on the current consumed by the laser line generator, additional drive circuitry in the form of a relay or solid state switch (e.g., BJT or MOSFET) may be necessary to source adequate power to the laser line generator 56 and laser line generator module 38.

In a preferred embodiment, when the visual cueing is activated, the laser line is turned on and projected by the laser line generator 56 just in front of the individual's feet, i.e., in a position in front of the walker 8. Under control of the laser line generator module 38 by the microcontroller 24, the laser line from the laser line generator 56 is then swept forward away from the individual to a point that does not exceed the individual's stride. As with the other parameters, this entry (data relating to the individual's stride) may be defined via the remote device 50 and stored in EEPROM, as are parameters relating to the manner in which the laser line sweeps forward, notably the rate that the laser line is swept forward. At the most forward point of the sweep, the laser line may be blanked (turned off) and the laser quickly returns to its initial position ready to repeat this process for the number of cycle times as defined in the EEPROM. Data relating to the manner in which the laser line is generated by the laser line generator module 38 is part of the content stored in the memory component and accessed by the microcontroller 24 when determining how and when to generate the visual cueing.

Figure 4B:
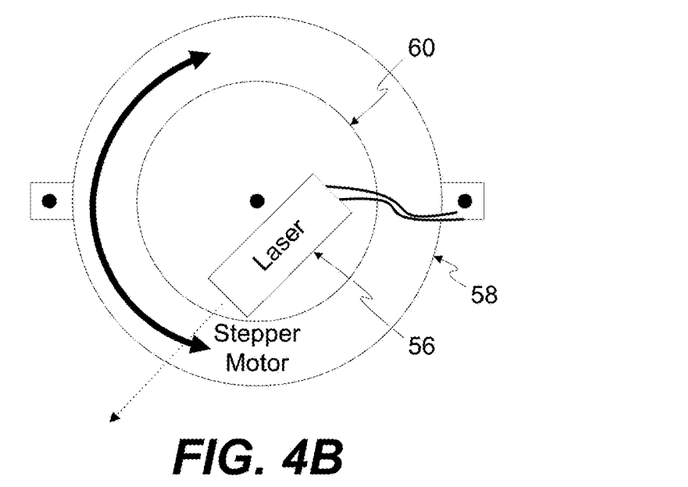
FIG. 4B and FIG. 4C reflect ways for providing sweeping visual cue line.

A stepper motor 58 (part of the laser line generator module 38) provides the motion for the laser line generator 56 as shown in FIG. 4B. The stepper motor 58 may be fastened to the enclosure of the enhanced cueing control unit 10. A shaft of the stepper motor 58 is affixed to a turntable 60 to which the laser line generator 56 is attached. As pulses are applied to the stepper motor 58 to advance the shaft and turntable 60 counter clockwise (CCW), the laser line will move away from the individual's feet. When pulsed in the opposite direction (clockwise or CW), the laser will move toward the individual. The turntable 60 may be operated in an open loop fashion after alignment from the factory or may be optionally equipped with limit switches, potentiometer or similar positional feedback hardware.

An 'H' bridge or similar circuit (part of the actuator/stepper drive control 42) is used as the drive control for the stepper motor 58 to source high drive current along with the ability to step the motor in either direction. Readily available stepper motors increment about 1.8 degrees per step, which equates to about 200 steps per revolution. Since the arc in which the turntable 60 moves the laser line generator is small relative to its full rotation capacity, a preferred embodiment includes gear reduction to reduce the step per pulse resolution to provide a smoother movement of the laser line sweep.

Figure 4C:
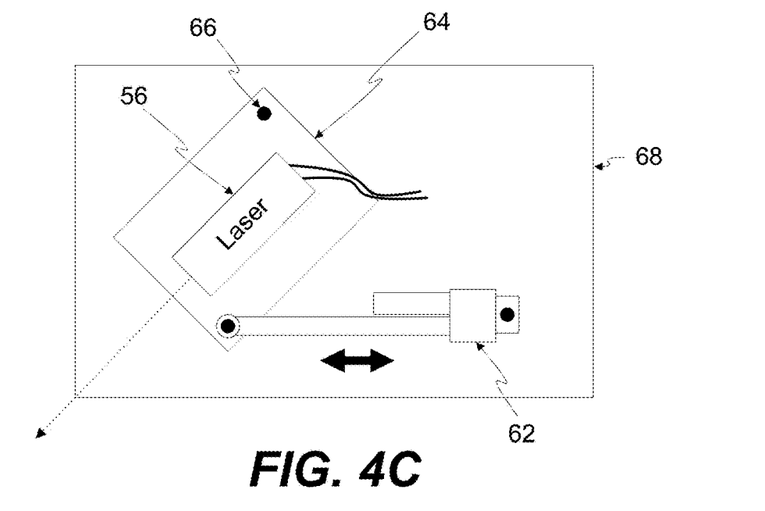

In an alternate embodiment, a linear actuator 62 provides the motion for the laser line generator 56, as shown in FIG. 4C. The linear actuator 62 may be fastened to the enclosure of the enhanced cueing control unit 10, e.g., the housing of which part is represented by 68. The actuator shaft may be affixed to the bottom of a plate 64 to which the laser line generator 56 is attached. The plate 64 hangs from a pivot point 66 at the top corner of the plate 64. An 'H' bridge or similar circuit is used as the drive control for the linear actuator 62 to source high drive current along with the ability to extend/retract the linear actuator 62 (in the direction of the arrow). As the actuator shaft is commanded to retract, the laser line generated by the laser line generator 56 will move away from the individual's feet. When commanded to extend, the laser will move toward the individual. Typically, linear actuators are equipped with limit switches to prevent being commanded beyond the physical bounds of their design.

In yet another embodiment, instead of a swept laser line, the laser line can be gated (turned on and then off) at fixed intervals within the arc and can be realized with either the stepper motor 58 or linear actuator 62 implementations shown in FIGS. 4B and 4C, respectively. In this embodiment, a sequence of laser lines are projected at fixed intervals that start at the individual's feet and incrementally move away from the individual's feet. The sweeping arc motion would be implemented in a manner similar to that described above with the exception that during the laser gating, movement would be paused momentarily to provide a more stable projection of the laser line so it appears in a static position rather than moving. The gate time/sweep pause time interval is a parameter that is defined via the remote device 50 and stored in EEPROM. At the most forward point of the sweep, the laser line is blanked (turned off) and the laser quickly returns to its initial position ready to repeat this process for the number of cycle times defined as in the prior embodiments.

Figure 5:
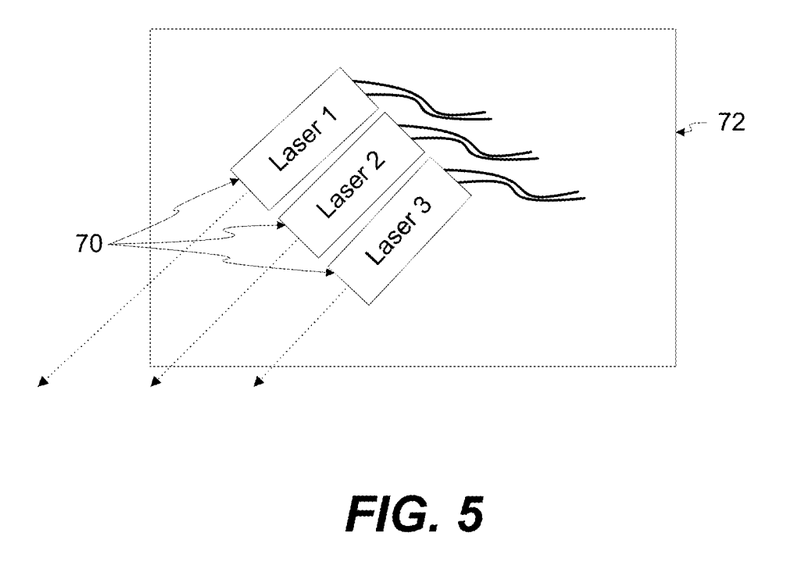
FIG. 5 reflects a manner for providing a series of different colored visual cue lines.

In yet another embodiment shown in FIG. 5, the laser line generator module 38 comprises a plurality of individual laser line generators 70 that are attached to a common substrate 72, such as a frame, housing or plate, which may be part of the enclosure of the enhanced cueing control unit 10 or separately attached to the frame 6 at a different location. The laser line generators 70 should be mounted in a position on the frame 6 to enable them to individually project a laser line in front of the user of the walker 8. For the sake of clarity, three (3) laser line generators 70 are shown alongside one another on the housing part 72 but the invention is not in any way limited to three (3) laser line generators 70, and any number of multiple laser line generators 70 may be used in this embodiment.

Laser line generators 70 are available in several colors including, but not limited to: red, green, blue and violet. In this embodiment, each of the laser line generators 70 is sequentially gated, under control of the microcontroller 24, to generate and project a series of laser lines without the need for movement of the laser line generators 70. In a preferred embodiment of this variant, each of the laser line generators 70 (designated Laser1, Laser 2, Laser 3) utilizes different colors (e.g., green, blue, red) to provide visual stimulation to the brain that is not afforded by a single monochromatic color of a laser line.

Each of the laser line generators 70 has an inherent spacing by placing them next to each other as shown in FIG. 5. The inner or intermediate laser line generator 70 (designated Laser 2) can have a fixed mounting position whereas the upper (designated Laser 1) and lower (designated Laser 3) laser line generator 70 have a slight angular offset that can be manually adjusted using slotted mounting holes to provide the spacing that is appropriate for a particular individual's stride.

Any time a laser is in use, there should be concerns for eye safety. In preferred embodiments, all laser line generators 56, 70 would be contained within the enhanced cueing control unit 10 enclosure rather than mounted externally to provide a certain level of protection to the laser line generator modules. Under normal operating conditions, a laser line generator 56, 70 would be pointing at the ground. In the unlikely event of a trip or fall, there is the possibility that the wheeled walker 8 could significantly tilt or even overturn. In this circumstance, the laser line generator 56, 70 could potentially be aimed directly at the faces/eyes of people nearby.

To prevent a hazardous situation such as this, a preferred embodiment utilizes a three axis accelerometer 36 to sense the initial state of the wheeled walker 8. The X, Y and Z components are determined at the time of power application and compared against expected limits (e.g., ±20 degree offset on any axis) as a sanity check. The accelerometer 36 thus senses or determines from measurements the initial state of the frame 6, and then may be used to determine the current state of the frame 6 whenever a laser line generator 56, 70 is sought to be activated to provide visual cueing. The accelerometer 36 provides to the microcontroller 24 the current measurements (or data derived therefrom) to allow the microcontroller to assess the state of the walker 8. The microcontroller 24 may compare the current state of the walker 8 to the initial state of the walker 8 and permit initiation of or initiate a laser line generator 56, 70 only when the current state of the walker 8 does not deviate from the initial state of the walker 8 beyond a predetermined angular offset.

For example, prior to gating or turning on a laser line generator 56, 70, the X, Y and Z components sensed by the accelerometer 36 would be polled by the microcontroller 24 to insure the wheeled walker 8 has not tipped or flipped over prior to turning on one of the laser line generators 56, 70. This is assessed based on the angular data provided by the three axis accelerometer 36. In this manner, the risk for aiming a laser line generator 56, 70 into the air and creating a potentially hazardous condition is mitigated. The three axis accelerometer 36 may also be used to augment the range distancing function as necessary. Instead of a three axis accelerometer, any other component or system may be used that is able to provide angular data about the walker 8 or its frame 6 to enable an assessment of the current state of the walker 8 relative to its initial, presumed normal, state.

One additional element of the enhanced cueing system involves audio and/or tone generation via the audio and/or tone generator 46. In one embodiment of the present invention, a plurality of tones are produced by the audio and/or tone generator 46 in a possibly known series such as Do-Re-Mi' or the root, third, fifth of a chord (e.g., notes C, E, G of major C chord) as the audio cueing. These tones could be generated by support hardware or even within the microcontroller 24 itself to accompany or substitute for the visual cueing by laser line generator module 38. In the embodiment that utilizes a plurality of laser line generators 70 (FIG. 5), these tones would be synchronized with the projection of the laser lines. Since walking speed (tempo) is unique to each individual, the speed of the sequence would also be a programmable parameter, e.g., via remote device 50.

The gain/amplifier component 48 serves to drive the speaker 44 within the enhanced cueing system so the individual can hear the audio cues. Output volume of the enhanced cueing system can be increased or decreased as necessary and is set through a parameter that is defined, for example, via the remote device 50 and stored in EEPROM.

Alternate embodiments may implement the ability to play pre-recorded audio files. These audio files could be generic in nature (e.g., 'take a step') or recorded by a family member so that there is a familiar voice. A pre-recorded audio file also has the benefit of avoiding potential language barriers as any phrase or sound can be utilized. Other hypotheses with respect to audible cueing involve sounds that would normally be associated with walking that the individual would try to imitate (e.g., the sound of military troops marching) or other pulsative sounds (e.g., the sound of shaking maracas) that invoke a stronger brain stimulus. Any tone sequence, audio file(s), tempo and related parameters would be uploaded via user control of the remote device 50 and stored in EEPROM.

In a preferred embodiment, the audio cueing output can be pre-empted, which is useful in the case of an emergency situation. In the event the wheeled walker 8 tipped over, the volume of the output from the speaker 44 could be increased to its maximum level and a piercing tone or audio file (e.g., 'Help!') could be looped to get the attention of nearby people for assistance as well.

In another preferred embodiment of the invention, the user control panel 26 is equipped with a 'Brake' pushbutton (see 28 in FIG. 3) that allows the individual using the walker 8 to apply/disengage the brakes of the wheeled walker 12 (also depicted schematically as 74 in FIG. 2). Individuals with festinating gait that can lead into accelerating gait are at high risk of falling over. In this embodiment, the 'Brake' pushbutton is used to engage the brakes 12 of the wheeled walker 8. Most wheeled walkers typically use a brake cable (also known as a Bowden cable) which comprises an inner stranded brake wire surrounded by an outer casing. Some wheeled walkers require applying tension to the inner cable to engage brakes whereas others require the release of tension to engage brakes.

Figure 6A:
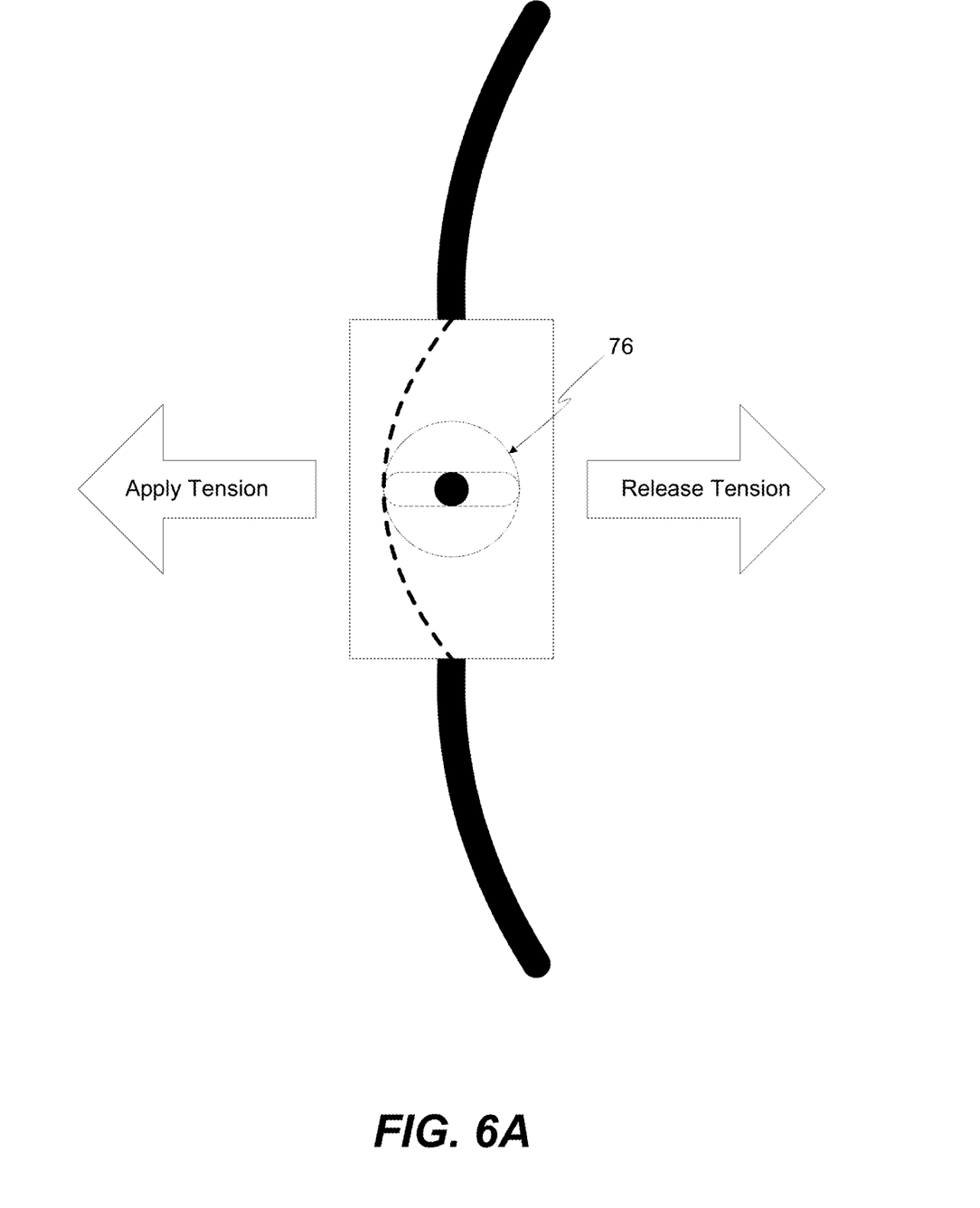
FIG. 6A and FIG. 6B illustrate methods of applying brakes.

The inline braking mechanism or braking system shown in FIG. 6A would be installed at a location on the wheeled walker structure or frame 6 slightly lower than the individual's waist where there is access to the brake cable(s) of the brakes 12. The outer casing of the brake cable would be cut/truncated with the mechanism inserted at the cut point. The inner wire would pass over the wheel 76 which is restricted to move orthogonally from the plane of the wire's entry/exit. To apply tension, the wheel 76 would be pulled further outward (i.e., to the left in FIG. 6A) increasing the length of the wire; whereas to release tension, the wheel would be pulled further inward (i.e., to the right in FIG. 6A) decreasing the length of the wire.

Figure 6B:
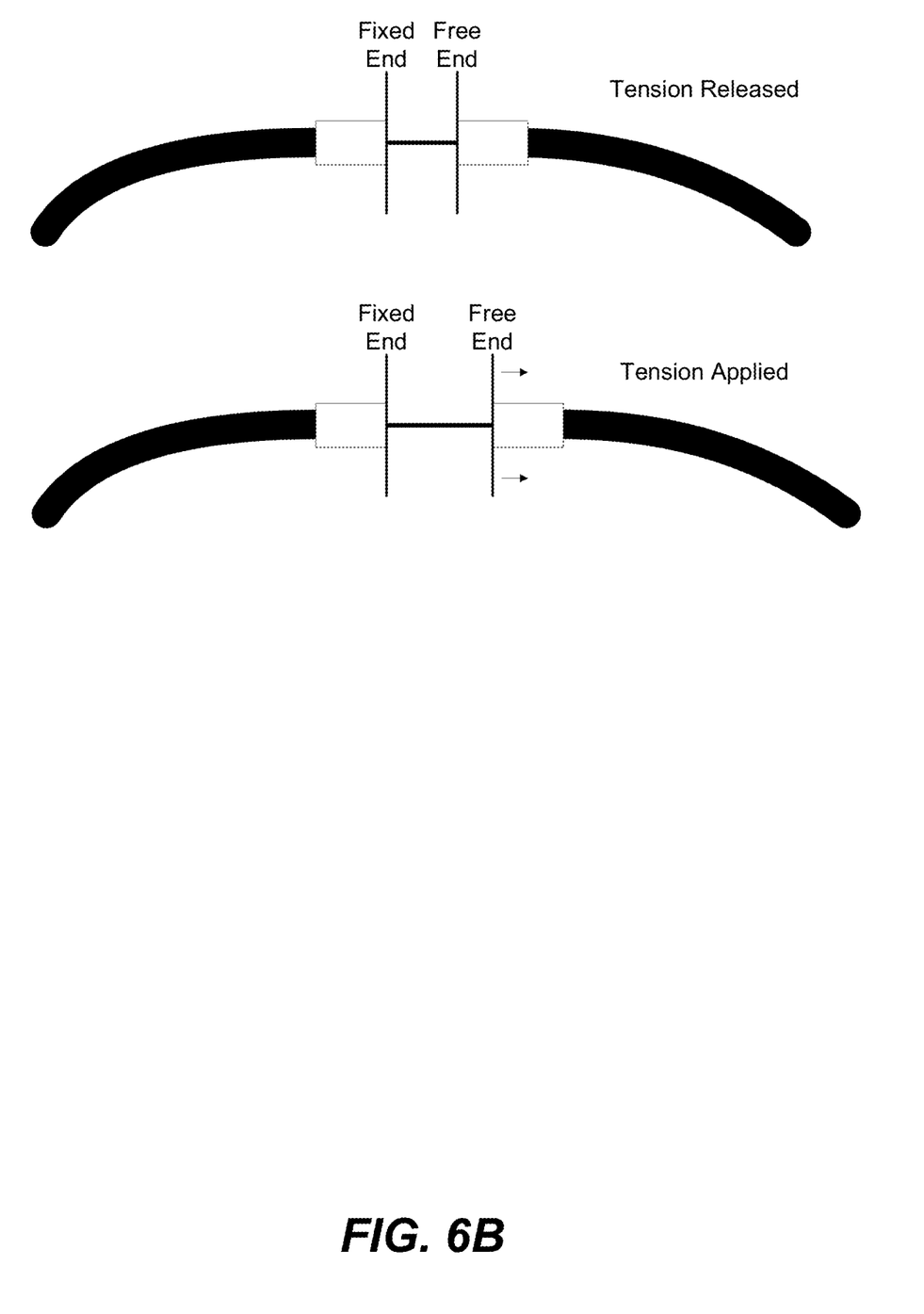

In an alternate embodiment shown in FIG. 6B, the outer casing of the brake cable would be cut and one end of the cable attached (fixed end) to the wheeled walker structure or frame 6. The other end of the cable (free end) would either be pulled axially away from the fixed end to apply tension or pulled towards the fixed end to release tension. Decreasing the distance of separation of the outer casing has the same effect of relaxing the inner brake wire (effectively lengthening the length of the inner wire relative to the outer casing).

Movement of the wheel 76 in FIG. 6A or free end of the cable in FIG. 6B would be through the use of a linear actuator/driver (part of the schematically depicted brake system 74 in FIG. 2) in a manner similar to what was used for visual cue movement (laser line(s) movement). Alternate embodiments may utilize direct electrically actuated brakes or even hydraulic brakes similar to those of a high end mountain bicycle. Regardless of the braking system type employed, the intent is the same; a pushbutton 28 (on control panel 26, see FIG. 3) could be used to engage the brake system 74 in the event the individual feels he/she is in imminent danger of falling over. The pushbutton requires minimal effort by the individual using the walker, as opposed to requiring the individual to squeeze a lever or otherwise cause tension to be manually applied to the cable of the braking system which could pose a challenge to an individual in frail health and gripped with the fear of falling. In an effort to maintain the minimalist interface, and to avoid a confusing array of buttons, the same pushbutton 28 on control panel 26 could be used to engage/disengage the brakes 12. Thus, the braking system has a first state allowing movement of the frame 6 and a second state preventing movement of the frame 6 and is switchable from the first state to the second state based on input other than manual adjustment of tension of a cable of the braking system, e.g., by depression of the pushbutton 28 on user control panel 26.

Instead of a pushbutton, an advanced braking control system may be integrated into the enhanced cueing control system 10 described above, in that the microcontroller 24 would controls the braking system 74, as see in FIG. 2. A communications module, such as the NFC or PAN communications hardware 32, receives via at least one communications frequency transmissions to engage or disengage the braking system 74; the microcontroller 24 engages or disengages the braking system 74 based on the transmissions received by the communications module.

Additionally or alternatively, the range distancing module 34 may be used in a braking control system. In this embodiment, the microcontroller 24 analyzes the determined distance between the frame 6 and the object rearward of the frame 6 (presumed to be the individual using the walker 8) to detect the freezing of gait episode. When the FOG episode is detected, the microcontroller 24 disengages the braking system 74 and reengages the braking system 74 when the episode is determined to have subsided. Generally, the microcontroller 24 engages or disengages based on analysis of the determined distance between the frame 6 and the object rearward of the frame 6 (presumably the individual using the walker 8).

In a preferred embodiment of the braking actuator, the microcontroller 24 may implement a lockout period (e.g., 10 seconds) during which subsequent multiple presses of the 'Brake' pushbutton on control panel 26 would have no effect after the initial press and brake engagement. This prevents the brakes 12 from being engaged/disengaged in rapid succession and potentially avoids a dangerous situation for the individual. The lockout period could be one of the definable parameters uploaded via the remote device 50 and stored in EEPROM. This embodiment may also implement brake lock initiation by another individual (e.g., caregiver, family member) remotely using the NFC or PAN communications hardware 32 or even tied in with the range sensing hardware 34 for automatic application of the braking system.

An advantage of embodiments of the invention is that it may be mounted axially, in line with the user and seek to determine rhythmic cadence to sense movement. If gait changes over time, the software program is capable of adapting without the need for mechanical adjustment. Recent studies have shown continuous visual and/or audible cueing may be of greater benefit to an individual with Parkinson's disease.

Differing from prior art mentioned above, the invention does not use feedback in its traditional sense, i.e., information about reactions and modification or control of a process or system by its results to provide a response after and a result of something specific occurring. Rather, the invention uses visual and audible cueing (or prompting) to instigate a response whereas feedback is the reaction to a response.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and is not limiting. The invention is limited only as defined in the claims and equivalents thereto.

The invention claimed is:
1. A walker, comprising:
a frame;
a movement enabling system on said frame that enables said frame to be moved along a surface; and
a cueing system that generates at least one of audio and visual cues to guide a user of the walker in their movement of the walker,
said cueing system comprising:
 a distance detector that detects distance, during movement of said frame, between said frame and an object rearward of said frame at multiple times;
 a control unit coupled to said distance detector and that determines a rhythm or pattern of detected distances between said frame and the object rearward of said frame and that generates signals based on stored content relating to cue generation and the determined rhythm or pattern of detected distances between said frame and the object rearward of said frame;
 at least one cue generator that generates the at least one of audio and visual cues based on the signals generated by said control unit; and
 a communications module coupled to said control unit and that receives via at least one communications frequency transmissions to set or modify the stored content, said control unit setting or modifying the stored content based on the transmissions received by said communications module.

2. The walker of claim 1, wherein said communications module includes a near field communication (NFC) system or a personal area network (PAN) system.

3. The walker of claim 1, wherein the stored content comprises audio tracks that constitute audio cues and said at least one cue generator comprises an audio and/or tone generator that vocalizes one of the audio tracks based on the signals generated by said control unit.

4. The walker of claim 3, wherein said communications module receives via the at least one communications frequency transmissions to set the stored content by adding audio tracks.

5. The walker of claim 3, wherein said communications module receives via the at least one communications frequency transmissions to set a parameter of the vocalizing of the one of the audio tracks by said audio and/or tone generator.

6. The walker of claim 3, wherein said audio tracks include an audio track of a defined series of tones or the root, third and fifth notes of a chord.

7. The walker of claim 3, wherein said audio tracks include an audio track relating to movement or an audio track of a voice known to the user of the walker.

8. The walker of claim 1, further comprising an electricity source arranged on said frame, said cueing system being coupled to said electricity source and said at least one cue generator continuously generating the at least one of audio and visual cues when provided with electricity from said electricity source without requiring manual activation.

9. A walker, comprising:
a frame;
a movement enabling system on said frame that enables said frame to be moved along a surface;
a cueing system that generates at least one of audio and visual cues to enable a user of the walker to be guided in their movement of the walker,
said cueing system comprising:
a control unit that generates signals based on stored content relating to cue generation;
at least one cue generator that generates the at least one of audio and visual cues based on the signals generated by said control unit; and
a communications module coupled to said control unit and that receives via at least one communications frequency transmissions to set or modify the stored content, said control unit setting or modifying the stored content based on the transmissions received by said communications module; and
a detector coupled to said control unit and that detects a freezing of gait episode, said at least one cue generator generating the at least one of audio and visual cues only when said detector detects the freezing of gait episode.

10. The walker of claim 9, wherein said detector comprises a range distancing module that determines a distance between said frame and an object rearward of said frame, said control unit analyzing the determined distance to detect the freezing of gait episode.

11. The walker of claim 10, wherein said range distancing module comprises an ultrasonic transmitter that transmits ultrasonic waves in a direction rearward from said frame and an ultrasonic receiver that receives ultrasonic waves reflected from any object in a path of ultrasonic waves transmitted by said ultrasonic transmitter, said range distancing module determining the distance between said frame and the object based on time between transmission and reception of each ultrasonic wave.

12. The walker of claim 10, wherein said control unit analyzes the determined distance to detect the freezing of gait episode by analyzing changes over time in the determined distance between said frame and the object rearward of said frame.

13. The walker of claim 10, wherein said control unit determines a pattern of change in the distance between said frame and the object rearward of said frame based on multiple determinations of the distance between said frame and the object rearward of said frame, and detects the freezing of gait episode based on a deviation from the pattern.

14. The walker of claim 10, wherein said control unit determines a rhythm for the distance between said frame and the object rearward of said frame based on multiple determinations of the distance between said frame and the object rearward of said frame and data about the user of the walker provided in transmissions received by said communications module, and detects the freezing of gait episode based on a deviation from the rhythm or when lack of rhythmic movement exceeds a movement time threshold.

15. The walker of claim 14, wherein the stored content includes an initial set of parameters specific to the user of the walker.

16. The walker of claim 15, wherein said control unit modifies the initial set of parameters based on analysis of the determined distance between said frame and the object rearward of said frame.

17. The walker of claim 1, wherein said communications module receives via the at least one communications frequency transmissions to enable or disable said at least one cue generator, said control unit enabling or disabling said at least one cue generator based on the transmissions received by said communications module.

18. The walker of claim 1, wherein said at least cue generator comprises a laser line generator module that generates a laser line that constitutes a visual cue, said laser line generator module being arranged on said frame in a position in which the laser line generated by said laser line generator module is in front of said frame.

19. The walker of claim 18, wherein said laser line generator module provides a variable timing for forward movement of the laser line generated by said laser line generator module, the variable timing being part of the stored content.

20. The walker of claim 18, wherein said laser line generator module generates a sequence of laser lines at fixed intervals that move incrementally away from said frame according to the stored content.

21. The walker of claim 18, wherein said laser line generator module comprises a rotatable turntable and a laser line generator arranged on said turntable, said laser line generator and said turntable being controlled by said control unit to gate the laser line at fixed intervals with a variable timing for forward movement of the laser line generated by said laser line generator module, the variable timing being part of the stored content.

22. The walker of claim 18, wherein said laser line generator module comprises a plurality of laser line generators that are sequentially gated to generate a series of lines and each of said laser line generators generates a different color laser line.

23. The walker of claim 18, further comprising an accelerometer that senses an initial and current state of said frame and is coupled to said control unit, said control unit initiating said laser line generator only when the current state of said frame does not deviate from the initial state of said frame beyond a predetermined angular offset.

24. The walker of claim 1, further comprising a user control panel including an actuatable member that, when actuated, sends an alert to at least one remote alert receiving device.

25. The walker of claim 24, wherein said user control panel is coupled to said communications module and when said actuatable member is actuated, directs said communications module to send the alert to the at least one remote alert receiving device.

26. The walker of claim 24, wherein said actuatable member is actuated in a plurality of different ways and depending on how said actuatable member is actuated, sends a plurality of different alerts to the at least one remote alert receiving device.

27. The walker of claim 1, further comprising:
a sound generating module; and
a user control panel including an actuatable member that, when actuated, is indicative of an emergency situation involving the user of the walker and causes said sound generator generating module to sound an audible alarm.

28. The walker of claim 27, wherein said cueing system is configured to sends messages to at least one remote alert receiving device when said actuatable member is actuated.

29. The walker of claim 1, wherein said distance detector comprises an ultrasonic transmitter that transmits ultrasonic waves in a direction rearward from said frame and an ultrasonic receiver that receives ultrasonic waves reflected from any object in a path of ultrasonic waves transmitted by said ultrasonic transmitter, the distance between said frame and the object rearward of said frame being based on time between transmission and reception of each ultrasonic wave.

30. The walker of claim 1, wherein said control unit generates signals based on stored content relating to cue generation, the determined rhythm or pattern of detected distances between said frame and the object rearward of said frame; and data about the user of the walker provided in transmissions received by said communications module.

31. The walker of claim 1, wherein the stored content includes an initial set of parameters specific to the user of the walker.

32. The walker of claim 1, wherein said cueing system generates the at least one of audio and visual cues during movement of the walker.

* * * * *

UNITED STATES PATENT AND TRADEMARK OFFICE
CERTIFICATE OF CORRECTION

| | |
|---|---|
| PATENT NO. | : 10,588,814 B1 |
| APPLICATION NO. | : 16/008257 |
| DATED | : March 17, 2020 |
| INVENTOR(S) | : Richard Engel and Eli Levi |

Page 1 of 1

It is certified that error appears in the above-identified patent and that said Letters Patent is hereby corrected as shown below:

In the Claims

Claim 27, Column 19, Line 24, delete "generator".

Signed and Sealed this
Fifth Day of May, 2020

Andrei Iancu
*Director of the United States Patent and Trademark Office*